United States Patent
Kang

(10) Patent No.: US 11,000,398 B2
(45) Date of Patent: May 11, 2021

(54) FLEXOR HINGE ORTHOSIS AND WRIST-DRIVEN FLEXOR HINGE ORTHOSIS

(71) Applicant: Yeoun Seung Kang, Seoul (KR)

(72) Inventor: Yeoun Seung Kang, Seoul (KR)

( * ) Notice: Subject to any disclaimer, the term of this patent is extended or adjusted under 35 U.S.C. 154(b) by 271 days.

(21) Appl. No.: 16/389,341

(22) Filed: Apr. 19, 2019

(65) Prior Publication Data

US 2020/0330254 A1 Oct. 22, 2020

(51) Int. Cl.
| | |
|---|---|
| *A61F 5/01* | (2006.01) |
| *A61H 1/02* | (2006.01) |
| *A63B 23/16* | (2006.01) |
| *A63B 21/045* | (2006.01) |
| *A63B 21/02* | (2006.01) |

(52) U.S. Cl.
CPC ............ *A61F 5/013* (2013.01); *A61H 1/0288* (2013.01); *A63B 21/025* (2013.01); *A63B 21/0455* (2013.01); *A63B 23/16* (2013.01); *A61F 2005/0179* (2013.01); *A61H 2201/1638* (2013.01)

(58) Field of Classification Search
CPC ............ A61F 5/013; A61F 2005/0179; A61H 1/0288; A61H 2201/1638; A61H 2205/065; A61H 2201/1207; A61H 1/0285; A61H 1/00; A63B 23/16; A63B 21/0455; A63B 21/025; A63B 21/023; A63B 23/14; A63B 2220/80; A63B 2220/51; A63B 2220/54; A63B 2225/09
See application file for complete search history.

(56) References Cited

U.S. PATENT DOCUMENTS

| | | | | |
|---|---|---|---|---|
| 5,876,363 | A * | 3/1999 | Marx | A61F 5/0118 602/21 |
| 7,001,352 | B2 * | 2/2006 | Farrell | A63B 23/16 602/21 |
| 8,603,018 | B2 * | 12/2013 | Anglada | A61F 5/013 602/21 |
| 9,757,266 | B2 * | 9/2017 | Hoffman | A61N 1/36031 |
| 10,758,394 | B2 * | 9/2020 | Kelly | A61H 1/02 |
| 10,849,767 | B1 * | 12/2020 | Blasse | A61F 2/583 |
| 2003/0162634 | A1 * | 8/2003 | Farrell | A63B 23/16 482/47 |
| 2003/0195093 | A1 * | 10/2003 | White | A63B 21/4025 482/124 |

(Continued)

OTHER PUBLICATIONS

Kang, et al., "Biomechanical evaluation of wrist-driven flexor hinge orthosis in persons with spinal cord injury", *JJRD*, vol. 50, No. 8, 2013, pp. 1129-1138.

(Continued)

*Primary Examiner* — Garrett K Atkinson
(74) *Attorney, Agent, or Firm* — Kilpatrick Townsend & Stockton LLP

(57) ABSTRACT

A flexor hinge orthosis comprises a forearm frame; a first frame connected to the forearm frame to be rotatable about a first rotation axis that extends in a lateral direction; a second frame configured to be fixed to a palmar of a user and connected to the second frame to be rotatable about a second rotation axis that extends in an upward-and-downward direction; a thumb frame; an operating lever; an actuating lever; an actuating rod; and a finger frame.

18 Claims, 5 Drawing Sheets

(56) References Cited

U.S. PATENT DOCUMENTS

| | | | |
|---|---|---|---|
| 2006/0211964 A1* | 9/2006 | Farrell | A61F 5/0118 602/5 |
| 2009/0149790 A1* | 6/2009 | Farrell | A61F 5/0118 602/20 |
| 2011/0077569 A1* | 3/2011 | Anglada | A61F 5/013 602/21 |
| 2012/0059298 A1* | 3/2012 | Hoffman | A61F 5/013 602/21 |
| 2014/0172166 A1* | 6/2014 | Kim | B25J 9/1697 700/259 |
| 2015/0148728 A1* | 5/2015 | Sallum | A61F 5/013 602/22 |
| 2016/0287422 A1* | 10/2016 | Kelly | A61H 1/02 |
| 2019/0175376 A1* | 6/2019 | Peisner | A61H 1/0274 |
| 2020/0360169 A1* | 11/2020 | Kelly | A61H 1/02 |

OTHER PUBLICATIONS

Johanson, et al., "The unoperated hand: the role of passive forces in hand function after tetraplegia", Hand Clinics, 18, 2002, pp. 391-398.

Tuijl, et al., "Evaluation of upper extremity motor function tests in tetraplegics", Spinal Cord, 2002, 40, pp. 51-64.

Rudhe, et al., "Upper extremity function in persons with tetraplegia: relationships between strength, capacity, and the spinal cord independence measure", Neurorehabilitation and Neural Repair, vol. 23, No. 5, 2009, pp. 413-421.

Rogers, et al, "Traumatic quadriplegia: follow-up study of self-care skills", Arch Phys Med Rehabil, vol. 61, Jul. 1980, pp. 316-321.

Knox, et al., "Results of a survey on the use of a wrist-driven splint for prehension", The American Journal of Occupational Therapy, vol. 25, 1971, No. 2, pp. 109-111.

Allen, et al., "Follow-up study of wrist-driven flexor-hinge-splint use", The American Journal of Occupational Therapy, 1971, vol. 25, No. 8, pp. 420-422.

Shepherd, et al., "Tenodesis brace use by persons with spinal cord injuries", The American Journal of Occupational Therapy, 1991, vol. 45, pp. 81-83.

Sargant, et al., "Occupational therapy management of the acute spinal cord-injured patient", The American Journal of Occupational Therapy, May 1986, vol. 40, pp. 333-337.

Moore, et al., An alternative technique for fabricating flexor hinge hand orthoses using total contact molded plastic finger pieces, Clinial Prosthetics and Orthotics, vol. 10, No. 3, pp. 115-118.

Nicket, et al., "Development of useful function in the severely paralyzed hand", The Journal of Bone and Joint Surgery, vol. 45-A, No. 5, Jul. 1963, pp. 933-952.

McKenzie, Mary W., "The ratchet handsplint", The American Journal of Occupational Therapy, Nov.-Dec. 1973, vol. 27, No. 8, pp. 477-479.

Barber et al., "Carbon dioxide-powered arm and hand devices", The American Journal of Occupational Therapy, May-Jun. 1969, vol. 23, No. 3, pp. 215-225.

Engen, et al., "Development of externally powered upper extremity orthotic systems"; The Journal of Bone and Joint Surgery, vol. 47B, No. 3, Aug. 1965, pp. 465-468.

Engen, et al., "Restoration of function in upper extremities by external power"; Archives of Physical Medicine and Rehabilitation, vol. 14, 1966, pp. 182-189.

Lehneis, et al., "Application of External Power of Orthotics", Orthotics and Prosthetics, Sep. 1968, pp. 34-45.

Mulcahey, et al., "Upper limb orthoses for the person with spinal cord injury", AAOS Atlas of Orthoses and Assistive Devices, Fourth Edition, Chapter 15, pp. 203-217.

Thorsen, et al., "Functional electrical stimulation reinforced tenodesis effect controlled by myoelectric activity from wrist extensors", JJRD, vol. 43, No. 2, Mar./Apr. 2006, pp. 247-256.

Mangold, et al., "Transcutaneous functional electrical stimulation for grasping in subjects with cervical spinal cord injury", Spinal Cord, 2005, vol. 43, pp. 1-13.

Crema, et al., "A hybrid tool for reaching and grasping rehabilitation: the ArmeoFES", 33$^{rd}$ Annual International Conference of the IEEE EMBS, Boston, MA,, 2011, pp. 3047-3050.

Saxena, et al, "An EMG-controlled grasping system for tetraplegics", Journal of Rehabilitation Research and Development, vol. 32, No. 1, Feb. 1995, pp. 17-24.

Hart, et al., "A comparison between control methods for implanted FES hand-grasp systems", IEEE Transactios on Rehabilitation Engineering, vol. 6. No. 2, Jun. 1998, pp. 208-218.

Hamou, et al., Pinch and elbow extension restoration in people with tetraplegia: a systematic review or the literature, JHS, vol. 34A, Apr. 2009, pp. 692-699.

Cizmar, et al., "Possible restorations of the upper extremity motion in tetraplegic patients—5-year clinical experience", Biomed Pap Med Fac Univ Palacky Olomouc Czech Repub., 2006, 150(2), pp. 313-319.

Reinholdt, et al., Rebalancing the tetraplegic wrist using extensor carpi ulnaris-tenodesis, The Journal of Hand Surgery (European Volume), vol. 38, No. 1, 2012, pp. 22-28.

Sabine, et al., "A plastic tenodesis splint", Orthopedic & Prosthetic Applicance Journal, Jun. 1965, pp. 137-140.

Bacon, et al., "Sequential advancing flexion retention attachment, A locking device for the wrist-driven flexor hinge splint", The American Journal of Occupational Therapy, Oct. 1978, vol. 32, No. 9. pp. 577-579.

Sabine, et al., "Report of development of the RIC plastic tenodysis splint", Archives of Physical Medicine & Rehabilitation, Dec. 1959, pp. 513-515.

Rosen, et al. "The team approach to orthotic management in quadriplegia", Clinical Prosthetics and Orthotics, vol. 11, No. 4. pp. 201-209, 1987, pp. 201-209.

Nichols, et al., "The value of flexor hinge hand splints", Prosthetics and Orthotics International, 1978, vol. 2, pp. 86-94.

Maynard, et al., "International standards for neurological and functional classification of spinal cord injury", Spinal Cord, 1997, vol. 35, pp. 266-274.

Hislop, et al., "Daniels & Worthingham's Muscle Testing, Techniques of Manual Examination, 8$^{th}$ Edition", Saunders, Elsevier, Missouri, 2007.

Mathiowetz et al., "Grip and Pinch Strength: Normative Data for Adults", Arch Phys Med Rehabil. 1985, vol. 66, pp. 69-72.

Pryce, "The Wrist Position Between Neutral and Ulnar Deviation that Facilitates the Maximum Power Grip Strength", J. Biomechanics, 1980, vol. 13, pp. 505-511.

Perotto, "Anatomical Guide for the Electromyographer, the Limbs and Trunk", Fifth Edition, (2011), Charles C Thomas Publisher, Ltd., Springfield, Illinois.

Stenehjem et al., "Wrist Driven Flexor Hinge Orthosis: Linkage Design Improvements", Arch Phys Med Rehabil, vol. 64, Nov. 1983, pp. 566-568.

Johnson, Radial Deviation Modification to the Wrist Driven Flexor Hinge Orthosis, Journal of Prosthetics and Orthotics, vol. 2, No. 4, pp. 305-308.

Bottlang et al., "Articulated external fixation of the ankle: minimizing motion resistance by accurate axis alignment", Journal of Biomechanics, vol. 32, 1999, pp. 63-70.

Lehneis, "Brace Alignment Considerations" Orthopedic & Prosthetic Appliance Journal, Jun. 1964, pp. 110-114.

Brumfield et al., "A Biomechanical Study of Normal Functional Wrist Motion", Clinical Orthopedics and Related Research, No. 187, 1984, pp. 23-25.

Irani, "Upper Limb Orthoses", Physical Medicine & Rehabilitation, 1995, Ch. 16, pp. 321-332.

Smith, "Early Complications of Key Grip Hand Surgery for Tetraplegia", Paraplegia, 1981, vol. 19, pp. 123-126.

* cited by examiner

FLEXOR HINGE ORTHOSIS AND WRIST-DRIVEN FLEXOR HINGE ORTHOSIS

TECHNICAL FIELD

The present disclosure relates to a flexor hinge orthosis for persons with spinal cord injury.

BACKGROUND

Promoting functional hand activities is a crucial rehabilitation goal for persons with tetraplegic spinal cord injury (SCI). Some people with mid- to low-level cervical (C) SCI achieve useful tenodesis grasp, which is opposition of the thumb and the index and middle fingers through reciprocal wrist extension and finger flexion, with the aid of a wrist-driven flexor hinge orthosis (WDFHO). Generally, persons with C6 and C7 tetraplegia can use a WDFHO for a variety of daily activities, such as eating, dressing, using the toilet, grooming, and writing. The WDFHO enables persons with tetraplegic SCI to attain a functional tenodesis grasp that creates enough passive tension in the paralyzed thumb and finger flexor muscles (such as flexor pollicis longus, flexor digitorum superficialis, and flexor digitorum profundus) with active wrist extension by contraction of the innervated extensor carpi radialis brevis (ECRB) and extensor carpi radialis longus (ECRL). Therefore, the WDFHO is an aideal device for persons with C6 or C7 tetraplegia who have wrist extensors with muscle strength of grade 3 or above on the manual muscle test (MMT) and who have either flickers or no finger movement to furnish their prehension effectively.

Referring to FIGS. 1 and 2, The WDFHO is made up of three main components: finger, palmar, and forearm. These three components are hinged at the anatomical axes of the wrist and metacarpophalangeal (MCP) joints J1 and J2. The WDFHO operates on a two-hinge parallelogram system that converts actively controlled wrist extension to passive flexion of the fingers at the MCP joint J2, resulting in a three-point prehension or three-jaw chuck grasp in which the index and middle fingers move together toward the immobilized thumb. Conversely, when the wrist flexes actively or passively due to gravity, the MCP joint J2 extends and the fingers open. An adjustable actuating lever 50 at the wrist joint J1 determines the level of wrist extension, allowing the hand to open and close at varying degrees. The level of wrist extension needed is based on the size of the object to be grasped.

The flexor hinge orthosis (FHO) was originally designed to restore upper-limb function of persons with poliomyelitis. As the incidence of poliomyelitis decreased, researchers began to investigate the application of FHO to other populations with upper-limb paralysis, such as SCI, hemiplegia, and brachial plexus injury.

Variations of FHOs exist for persons with SCI who are unable to use the wrist extension functionally. Persons with high-level SCI who lack voluntary wrist extension and hand motion are suitable candidates for the ratchet FHO, the Mckibben FHO, the electric motor-driven FHO, and the shoulder harness-driven FHO.

The ratchet FHO is designed to push a ratchet lever until the fingers reach the desired position. To form a three-point prehension, the user must exert force on the lever to passively close the fingers by gross motion of the other hand or by pushing against any stationary object. When the ratchet button is tapped, the ratchet lock is opened and the grasp is released.

Two external power sources, compressed carbon dioxide ($CO_2$) gas or an electric motor, can also substitute for paralyzed wrist extensors in a second variation of the FHO. The $CO_2$ gas is used to inflate an artificial muscle, also referred to as the Mckibben muscle, which consists of an inner rubber tube and an outer helically woven fabric. When pressurized with $CO_2$, this flexible rubber "bladder" expands against the woven fabric and shortens in length like a real muscle. Inflation of the artificial muscle propels the fingers into flexion against the stable thumb, and grasp release after deflating the Mckibben muscle can be achieved by gravity, spring, or the pull of a rubber band. The electrical motor-driven FHO is powered by a rechargeable battery pack. It can be controlled by a switch, which the patient may activate using any available muscle. The electromyography (EMG) signal can proportionally control the electric motor using a microprocessor.

Finally, the Bowden cable system can be incorporated to activate three-point prehension in the shoulder harness-driven FHO. In this orthosis, the shoulder motion pulls the cable out of its housing and transfers power from the shoulder musculature to the FHO to release the grasp. Grasp closure is produced by a rubber band or flexor spring pull.

These four FHO variations are complex. These orthoses are subject to actuators' bulkiness, poor cosmesis, and donning issues and require more technical support and more sophisticated training programs than the WDFHO prototype operated by voluntary wrist extension.

Until now, other rehabilitative approaches also have been attempted to improve hand function in persons with tetraplegic SCI. Functional electrical stimulation (FES) enables persons with tetraplegia to restore grasp function. This system uses electrical current pulses to excite nerves going to paralyzed muscles and provokes contraction of the muscles required for grasp and release. In addition, reconstructive surgery can be performed to transfer active muscles or shorten tendons to enhance grasp force.

Despite the emergence of new technologies and evolution of upper-limb rehabilitation for persons with tetraplegia, the WDFHO still continues to be used to improve hand function because of its noninvasiveness, simplicity of design, relatively low cost, and easy availability in the market. However, little is known about the biomechanical properties of this orthosis. Most of the available studies for the WDFHO date from the 1960s to the mid-1980s and only discuss basic construction and structural modifications. Furthermore, the majority of information on using the WDFHO in clinical practice comes from protocols that various departments had written for their own use, and clinical reports in the literature rely heavily on questionnaires to evaluate the efficacy of the WDFHO. Thus, it is difficult to accurately assess the usefulness of the WDFHO and to clearly understand its function without a careful biomechanical analysis involving mechanical modeling of the operating principle. Given the limited information on biomechanical characteristics in the literature, additional biomechanical assessment for the WDFHO is imperative. The present inventors have evaluated the effectiveness of the WDFHO by providing quantitative biomechanical analysis of the orthosis.

SUMMARY

Various embodiments of the present disclosure provide a flexor hinge orthosis. In an embodiment, a flexor hinge orthosis according to an embodiment of the present disclosure includes: a forearm frame configured to be fixed to a forearm of a user; a first frame connected to the forearm frame to be rotatable about a first rotation axis that extends in a first lateral direction; a second frame configured to be fixed to a palmar of the user and connected to the first frame to be rotatable about a second rotation axis that extends in an upward-and-downward direction; a thumb frame fixed to the second frame and configured to be fixed to a thumb of the user; an operating lever connected to the second frame to be rotatable about a third rotation axis that extends in a second lateral direction; an actuating lever fixed to the forearm frame; an actuating rod having a first end connected to the actuating lever such that the first end is rotatable and a second end connected to the operating lever such that the second end is rotatable; and a finger frame configured to be fixed to an index finger of the user and connected to the operating lever.

In an embodiment, the first end of the actuating rod may be connected to the actuating lever to be rotatable about a rotation axis parallel to the first rotation axis and a rotation axis parallel to the second rotation axis.

In an embodiment, the second end of the actuating rod may be connected to the operating lever to be rotatable about a rotation axis parallel to the first rotation axis and a rotation axis parallel to the second rotation axis.

In an embodiment, the forearm frame and the first frame may be hinged at the first rotation axis of a wrist joint, the first frame and the second frame may be hinged at the second rotation axis of an additional joint, and the additional joint may be located at a distal side of the wrist joint.

In an embodiment, the first end of the actuating rod may be connected to the actuating lever to be rotatable about a rotation axis parallel to the first rotation axis and a rotation axis parallel to the second rotation axis, and the second end of the actuating rod may be connected to the operating lever to be rotatable about a rotation axis parallel to the first rotation axis and a rotation axis parallel to the second rotation axis.

In an embodiment, the flexor hinge orthosis may further comprise a torsion spring configured to be elastically deformed when the second frame rotates in a first rotation direction and to be elastically restored when the second frame rotates in a second rotation direction that is opposite to the first rotation direction. The first rotation direction is a rotation direction when a distal end of the second frame moves in radius-side direction.

In an embodiment, the flexor hinge orthosis may further comprise a spring configured to be elastically deformed when the second frame rotates in a first rotation direction and to be elastically restored when the second frame rotates in a second rotation direction that is opposite to the first rotation direction. The first rotation direction is a rotation direction when a distal end of the second frame moves in radius-side direction.

In an embodiment, the spring may be a torsion spring or a spiral spring.

In an embodiment, the spring may be a spiral spring that is configured such that a degree of winding of the spiral spring is adjustable by a user in a state in which the second frame does not rotate with respect to the first frame.

The flexor hinge orthosis may be a wrist-driven flexor hinge orthosis. Various embodiments of the present disclosure provide a wrist-driven flexor hinge orthosis.

BRIEF DESCRIPTION OF DRAWINGS

The accompanying drawings, which are incorporated in and constitute a part of the specification, illustrate embodiments of the present disclosure, and together with the general description given above and the detailed description of the embodiments given below, serve to explain the principles of the present disclosure.

DETAILED DESCRIPTION

Figure 1:
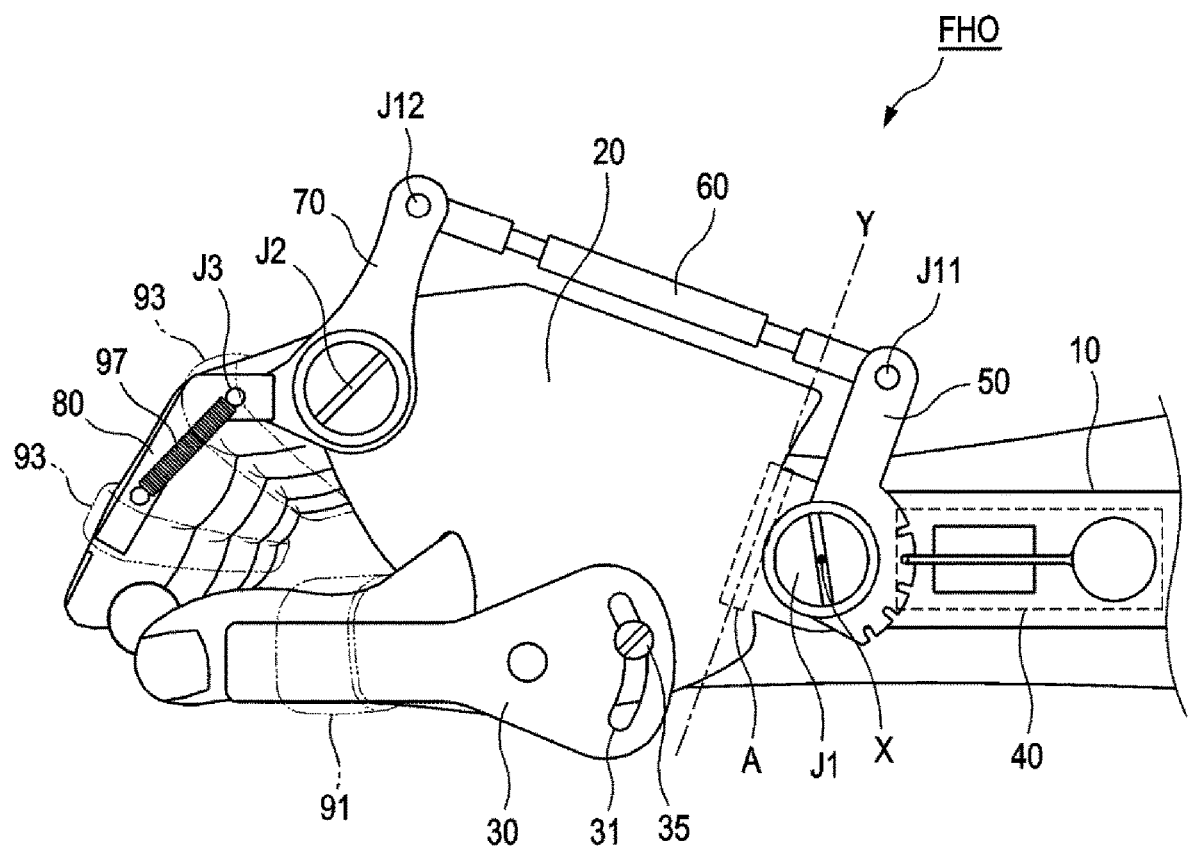
FIG. 1 is a perspective view showing a flexor hinge orthosis (FHO) structure and three-point prehension in example of right-hand side in the prior art.

Embodiments of the present disclosure are illustrated for the purpose of explaining the technical idea of the present disclosure. The scope of the rights according to the present disclosure is not limited to the embodiments presented below or the detailed descriptions of such embodiments.

All the technical terms and scientific terms in the present disclosure include meanings or definitions that are commonly understood by those of ordinary skill in the art unless otherwise defined. All terms in the present disclosure are selected for the purpose of describing the present disclosure more clearly, and are not selected to limit the scope of the present disclosure.

As used in the present disclosure, expressions such as "comprising," "including," "having," and the like are to be understood as open-ended terms having the possibility of encompassing other embodiments, unless otherwise mentioned in the phrase or sentence containing such expressions.

The singular expressions that are described in the present disclosure may encompass plural expressions unless otherwise stated, which will be also applied to the singular expressions recited in the claims.

The expressions, such as "first," "second," etc., which are shown in various embodiments of the present disclosure, are used to separate a plurality of elements from each other, and are not intended to limit an order or importance of the corresponding elements.

A forearm has a radius and an ulna, which are bones. Direction-indicating terms such as "lateral direction" used in the present disclosure indicate "radius-side direction" and "ulna-side direction". Direction-indicating terms such as "forward" and "distal" used in the present disclosure indicate a direction based on the direction in which a fingertip of an index finger is located with respect to a wrist in a state in which a user stretch the index finger, and thus direction-indicating terms such as "rearward" and "proximal" indicate the direction opposite thereto. Direction-indicating terms such as "upward" and "upper" used in the present disclosure indicate the direction which the back of the hand faces, and direction-indicating terms such as "downward" and "lower" indicate a direction opposite thereto.

The expression such as "rotation axis" means a virtual rotation axis for describing a joint or a connection relationship between two components.

Hereinafter, the embodiments of the present disclosure will be described in detail with reference to the accompanying drawings. The same reference numeral will be used for the same element throughout the drawings, and a duplicate description of the same element will be omitted.

The wrist-driven flexor hinge orthosis (WDFHO) is a device used to restore hand function in persons with tetraplegic spinal cord injury by furnishing three-point prehension. The present inventors assessed the effectiveness and biomechanical properties of the WDFHO in 24 persons with cervical 6 or 7 tetraplegia who have severely impaired hand function. The present disclosure introduces a mechanical operating model to assess the efficiency of the WDFHO. Experimental results showed that pinch force increased significantly ($p<0.001$) after using the WDFHO and was found to positively correlate with the strength of wrist extensor muscles ($r=0.41$, $p<0.001$). However, when the strength of the wrist extensors acting on the WDFHO was greater, the reciprocal wrist and finger motion that generates three-point prehension was less effective ($r=0.79$, $p<0.001$). Reliable and valid biomechanical evaluation of the WDFHO could improve our understanding of its biomechanics.

The present inventors recruited 24 persons with complete SCI (22 male and 2 female, 37.1±12.8 yr old [mean±standard deviation]) who have C6 or C7 American Spinal Injury Association Impairment Scale (AIS) grade A and paralysis or severe weakness of the hands. AIS classification was determined by medical chart review. Each patient had been injured for 5.6±7.3 yr at the time. To be eligible for participation, patients must have scored at least grade 3 (3/5) on an MMT for wrist extensor muscles. Patients with spasticity or contracture that interferes with hand grasp function were excluded.

Figure 2:
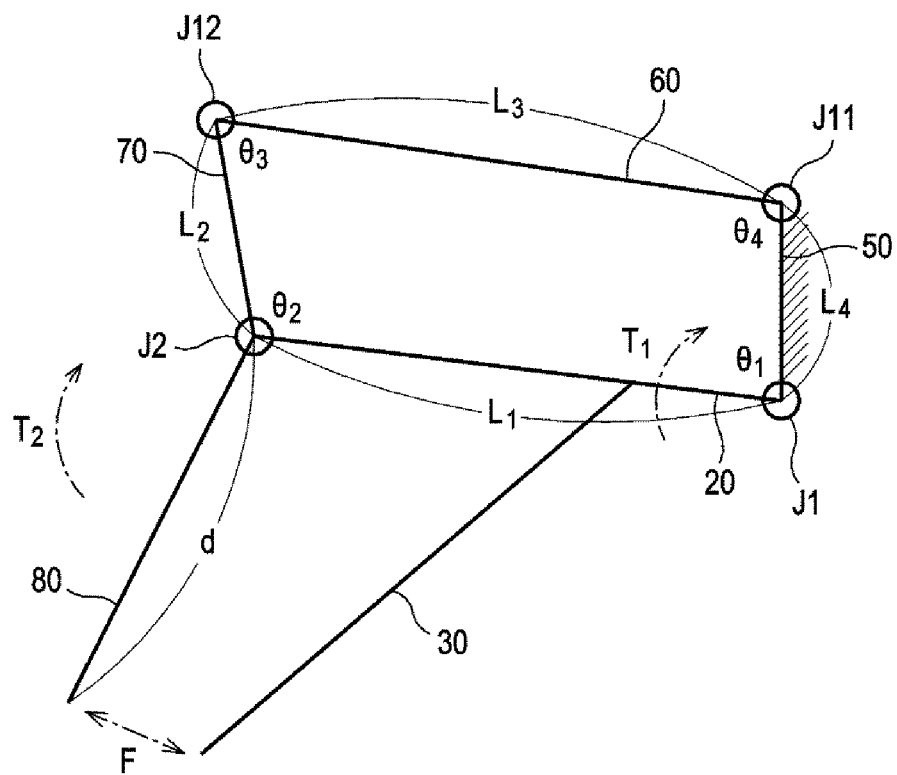
FIG. 2 is a schematic diagram of grasp motion with FHO according to the prior art in FIG. 1. d=length from radial side of MCP joint J2 to fingertip, F=three-point pinch force, L1=length from radial side of MCP joint J2 to distal tip of radial styloid, L2=length of operating lever, L3=length of actuating rod, L4=length of actuating lever, MCP=metacarpophalangeal, T1=wrist extension torque, T2=MCP joint torque, θ1-θ4=angles between four linkages.

The patients were fitted with an adjustable WDFHO (Talon™, North Coast Medical Inc; Gilroy, Calif.) consisting of a polyethylene forearm and a palmar cuff to grasp objects. This orthosis is a prefabricated device (FIGS. 1 and 2). The lengths of links L1 and L3 (FIG. 2) are adjustable to fit each subject from the radial side of the MCP joint J2 to the distal tip of the radial styloid and to match the subject's available range of motion (ROM) at the MCP joint J2. The interphalangeal (IP) joints of the index and middle fingers are stabilized along with the IP and MCP joints of the thumb. When a subject extends his or her wrist, the posted thumb and index and middle fingers are pushed together to attain a grasp motion. Conversely, wrist flexion causes the hand to open. There are five levels in the gear slot selector 40 that regulate the angle of wrist extension (FIG. 1). Pressing the spring-loaded button of the gear slot selector 40 locks the notched actuating lever 50 into the desired position. A certified orthotist and occupational therapist set up the WDFHO for each subject throughout the experiment.

FIGS. 1 and 2 show the WDFHO structure and corresponding schematic diagram for deriving static governing equations. In a typical WDFHO structure, the wrist extension torque (T1) is transferred to the MCP joint J2 through the four bar linkages system. The wrist extension torque (T1) rotates link 1 (L1) clockwise, which results in a counter-clockwise rotation of the operating lever 70 (L2). The resultant torque at the MCP joint J2 (T2) is balanced with the three-point pinch force (F) at the static pinch. The torque at the MCP joint J2 (T2) is determined from the geometry of the four bar linkages as the following (Equation (1)):

$$T_2 = \frac{L_2 \cos(90° - \theta_3)}{L_2 \cos(90° - \theta_3) + L_1 \sin(\theta_1 - \theta_4)} T_1$$

See Appendix (available online only) for detailed derivation.

Since T2 is equivalent to the pinch force (F) multiplied by the moment arm (d), the resultant pinch force is calculated as the following (Equation (2)):

$$F = \frac{L_2 \cos(90° - \theta_3)}{L_2 \cos(90° - \theta_3) + L_1 \sin(\theta_1 + \theta_4)} \times \frac{T_1}{d}$$

Subject hand sizes (lengths of thumb and fingers and lengths between wrist to MCP joints of thumb and fingers) were measured prior to the test in order to fit the WDFHO. A physician measured passive and active ROM of the wrist and hand joints and assessed the strength of wrist and hand muscles by using a MMT. Subjects were seated in their own wheelchairs and positioned into the most upright posture possible (hip, knee, and ankle joints angles at 90°). The subjects' dominant upper limbs were supported on the table with their shoulders adducted and neutrally rotated, elbow flexed at 90°, forearm in fully pronated position, wrist at 0° extension, and no radial or ulnar deviation. A cushion (2 in. thick) was placed under the wrist to provide enough room to flex the wrist joint J1. Two surface EMG electrodes (Shimmer; Dublin, Ireland) were attached two fingerbreadths distal to the lateral epicondyle to monitor ECRB and ECRL muscle activity during wrist extension. The three-point pinch force of each subject's dominant hand without the WDFHO was measured using a six degrees of freedom force transducer (Nano17 force/torque sensor, ATI Industrial Automation; Apex, N.C.). The WDFHO was fitted to the subject's dominant hand, and the wrist was extended to a selected level of the gear slot so that the subject could apply a maximum three-point pinch force while the force transducer measured the force. The maximum voluntary contraction (MVC) of the subject's wrist extensors was measured using a custom-made dynamometer, which consists of forearm and hand cuffs and a torque transducer (TRT 100, Transducer Techniques Inc; Temecula, Calif.). Each measurement was repeated three times, and the mean values were selected as the pinch force and MVC of the wrist extensors.

The mean pinch force of all 24 subjects was 0.64±0.42 N without using the WDFHO. The MMT for all hand muscles were grossly scored from grade 0 to 1. However, the MMT for wrist extensors were scored as at least grade 3 for all subjects. Of the 24 subjects, 14 were scored as grade 4 (wrist extension MVC: 1.92±0.82 Nm occurred at 29.4±11.5 wrist extension), 5 subjects had grade 3 (wrist extension MVC: 0.71±0.03 Nm occurred at 9.8±16.7 0 wrist extension), and 5 subjects had grade 3 (wrist extension MVC: 0.46±0.06 Nm occurred at 26.4±15.0 □ wrist extension).

The pinch force while using the WDFHO was calculated to be 7.26±3.48 N, which is 14.3±8.6 times greater ($p<0.001$) than the pinch force without the orthosis. The pinch force was significantly increased with the WDFHO, and greater MVC resulted in a greater pinch force increment ($r=0.41$) (Experimental procedure subject performing three-point pinch without using wrist-driven flexor hinge orthosis).

Ideally, the wrist extension MVC (T1) should be transferred to the pinch force (F) as defined by Equation (2). However, due to the friction and misalignment, T1 was not fully transferred to the pinch force. Torque transfer efficiency was calculated by dividing the actual pinch force measured with the WDFHO by the ideal pinch force calculated from the wrist MVC measurement. The ideal pinch force was calculated from Equation (2). The average efficiency was 37.6 percent, and the efficiency was greater for those subjects who had weaker wrist extensor strength (r=0.79) (Experimental procedure subject performing three-point pinch using WDFHO). However, the pinch efficiency was not significantly correlated with the wrist extension angle at MVC (r=0.07).

According to the present disclosure in some embodiments, a flexor hinge orthosis FHO may be one of an electric motor-driven FHO, a shoulder harness-driven FHO and a wrist-driven FHO. Desirably, the flexor hinge orthosis FHO may be the wrist-driven FHO.

FIG. 1 is a perspective view showing a flexor hinge orthosis (FHO) structure and three-point prehension in example of right-hand side in the prior art. FIG. 2 is a schematic diagram of grasp motion with FHO according to the prior art in FIG. 1. Hereinafter, referring to FIGS. 1 and 2, a flexor hinge orthosis FHO comprises a forearm frame 10 configured to be fixed to a user's forearm. The forearm frame 10 may be configured to be fixed to the forearm by a strap.

The flexor hinge orthosis FHO comprises a palmar frame 20 connected to the forearm frame 10 to be rotatable about a first rotation axis X that extends in a lateral direction. The palmar frame 20 is configured to be fixed to a user's palmar. The user can wear the palmar frame 20 on his or her palmar. For example, the palmar frame 20 may be configured to be fixed to the palmar by a strap and/or a hole that the thumb passes.

The flexor hinge orthosis FHO comprises a thumb frame 30 fixed to the palmar frame 20. The thumb frame 30 is configured to be fixed to a user's thumb. The thumb frame 30 may be configured to be fixed to the thumb by a strap 91. The thumb frame 30 is fixed to the palmar frame 20, but an angle between the palmar frame 20 and the thumb frame 30 can be adjusted by a slot 31 and a bolt 35.

The flexor hinge orthosis FHO comprises an operating lever 70 connected to the palmar frame 20 to be rotatable about a rotation axis parallel to the first rotation axis X. The operating lever 70 may include a first portion protruded in an upward direction from joint J2. One end of the first portion of the operating lever 70 is connected to the palmar frame 20, and the other end of the first portion of the operating lever 70 is connected to an actuating rod 60. The operating lever 70 may include a second portion that is protruded in a distal direction from joint J2. One end of the second portion of the operating lever 70 is connected to the finger frame 80, and the other end of the second portion of the operating lever 70 is connected to the palmar frame 20.

The flexor hinge orthosis FHO comprises an actuating lever 50 fixed to the forearm frame 10. The actuating lever 50 may protruded in an upward direction from joint J1. One end of the actuating lever 50 is connected to the palmar frame 20, and the other end of the actuating lever 50 is connected to the actuating rod 60.

The flexor hinge orthosis FHO comprises a gear slot selector 40. There are plural levels in the gear slot selector 40 that regulate the angle between the forearm frame 10 and the actuating lever 50. The gear slot selector 40 is configured to lock the notched actuating lever 50 into a predetermined position according to a user.

The flexor hinge orthosis FHO comprises an actuating rod 60. The actuating rod 60 has one end connected to the actuating lever 50 to be rotatable and the other end connected to the operating lever 70 to be rotatable. The one end of the actuating rod 60 is connected to the actuating lever 50 to be rotatable about a rotation axis parallel to the first rotation axis X. The other end of the actuating rod 60 is connected to the operating lever 70 to be rotatable about a rotation axis parallel to the first rotation axis X.

The flexor hinge orthosis FHO comprises a finger frame 80 configured to be fixed to a user's index finger. The finger frame 80 may be configured to be fixed to the index finger by a strap 93. The finger frame 80 may be configured to be fixed to the index finger with other finger(s) such as a middle finger. The finger frame 80 is connected to the operating lever 70. The finger frame 80 may be connected to the operating lever 70 to be rotatable about a rotation axis parallel to the first rotation axis X.

The flexor hinge orthosis FHO may comprises a spring 97. One end of the spring 97 may be fixed to a hinge joint J3 and the other end of the spring 97 may be fixed to a distal portion of the finger frame 80. The finger frame 80 and the spring 97 may be configured such that the user's fingertip of the index finger moves to the user's fingertip of the thumb when the spring 97 is elastically restored and the finger frame 80 rotates in about the rotation axis parallel to the first rotation axis X.

The forearm frame 10 and the palmar frame 20 are hinged at the first rotation axis X of a wrist joint J1. The palmar frame 20 and the operating lever 70 are hinged at a rotation axis, which is parallel to the first rotation axis X, of a joint J2. The actuating lever 50 and the actuating rod 60 are hinged at a rotation axis, which is parallel to the first rotation axis X, of a joint J11. The actuating rod 60 and the operating lever 70 are hinged at a rotation axis, which is parallel to the first rotation axis X, of a joint J12. The operating lever 70 and the finger frame 80 may be hinged at a rotation axis, which is parallel to the first rotation axis X, of a joint J3.

Figure 3:
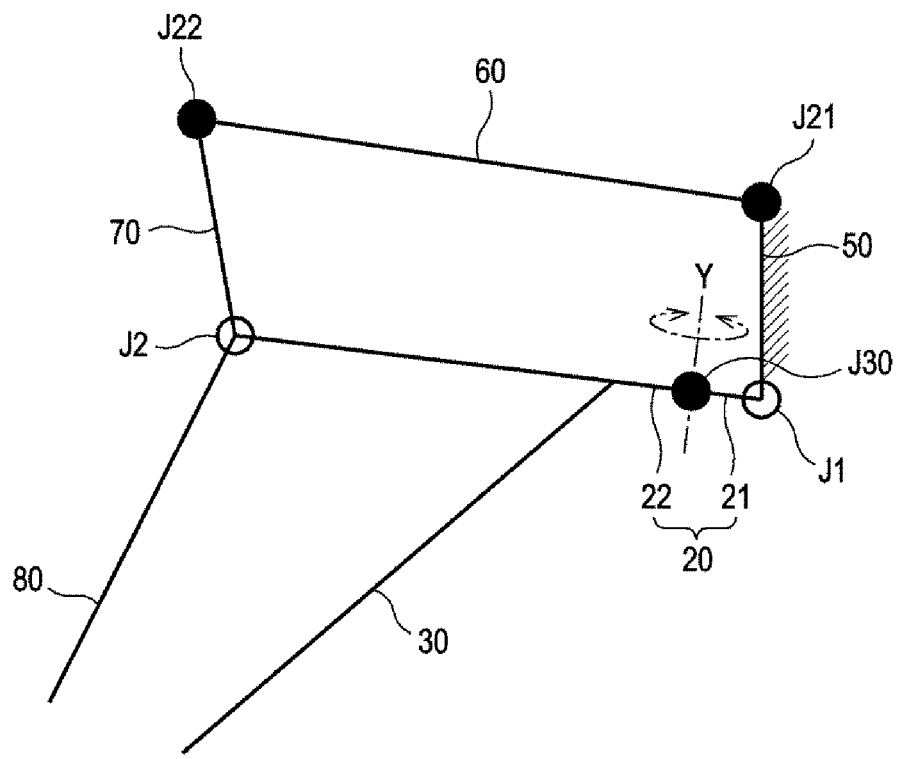
FIG. 3 is a schematic diagram of grasp motion with FHO according to an embodiment of the present disclosure.

FIG. 3 is a schematic diagram of grasp motion with FHO according to an embodiment of the present disclosure. Hereinafter, referring to FIG. 3, the flexor hinge orthosis FHO comprises a palmar frame. The palmar frame 20 comprises a first frame 21 connected to the forearm frame 10 to be rotatable about the first rotation axis X. The palmar frame 20 also comprises a second frame 22 connected to the first frame 21 to be rotatable about a second rotation axis Y that extends in an upward-and-downward direction. Accordingly, a user of the FHO can rotate his or her hand about the second rotation axis Y.

The second frame 22 is configured to be fixed to a user's palmar. The user can wear the second frame 22 on his or her palmar. For example, the second frame 22 may be configured to be fixed to the palmar by a strap and/or a hole that the thumb passes.

The flexor hinge orthosis FHO comprises a thumb frame 30 fixed to the second frame 22. The thumb frame 30 is configured to be fixed to a user's thumb. The thumb frame 30 may be configured to be fixed to the thumb by a strap. The thumb frame 30 is fixed to the second frame 22, but an angle between the second frame 22 and the thumb frame 30 can be adjusted by the slot and the bolt.

The flexor hinge orthosis FHO comprises a operating lever 70 connected to the second frame 22 to be rotatable about a third rotation axis that extends in a lateral direction.

The operating lever 70 may include a first portion protruded in an upward direction from joint J2. One end of the first portion of the operating lever 70 is connected to the second frame 22, and the other end of the first portion of the operating lever 70 is connected to an actuating rod 60. The operating lever 70 may include a second portion that is protruded in a distal direction from joint J2. One end of the second portion of the operating lever 70 is connected to the finger frame 80, and the other end of the second portion of the operating lever 70 is connected to the second frame 22.

According to the second frame's rotation position with respect to the first frame about the second rotation axis Y, the third rotation axis may be parallel to the first rotation axis X or angled with the first rotation axis X. The first rotation axis may extend in a first lateral direction, and the third rotation axis may extend in a second lateral direction. Further, according to the second frame's rotation position with respect to the first frame about the second rotation axis Y, the first lateral direction may be the same as the second lateral direction or may be angled with the second lateral direction.

The actuating lever 50 is fixed to the forearm frame 10. The actuating lever 50 may protruded in an upward direction from joint J1. One end of the actuating lever 50 is connected to the first frame 21, and the other end of the actuating lever 50 is connected to the actuating rod 60.

The flexor hinge orthosis FHO comprises the gear slot selector.

The flexor hinge orthosis FHO comprises an actuating rod 60 having one end connected to the actuating lever 50 to be rotatable and the other end connected to the operating lever 70 to be rotatable.

The one end of the actuating rod 60 may be connected to the actuating lever 50 to be rotatable about a rotation axis parallel to the first rotation axis X and a rotation axis parallel to the second rotation axis Y. The actuating rod 60 and the actuating lever 50 may be connected to each other by a universal joint (referring to FIG. 6).

The other end of the actuating rod 60 may be connected to the operating lever 70 to be rotatable about a rotation axis parallel to the first rotation axis X and a rotation axis parallel to the second rotation axis Y. The actuating rod 60 and the operating lever 70 may be connected to each other by a universal joint (referring to FIG. 6).

The flexor hinge orthosis FHO comprises a finger frame 80 configured to be fixed to a user's index finger. The finger frame 80 may be configured to be fixed to the index finger by a strap. The finger frame 80 may be configured to be fixed to the index finger with other finger(s) such as a middle finger. The finger frame 80 is connected to the operating lever 70. The finger frame 80 may be connected to the operating lever 70 to be rotatable about a rotation axis parallel to the third rotation axis.

The flexor hinge orthosis FHO may comprise the spring 97.

The forearm frame 10 and the first frame 21 are hinged at the first rotation axis X of a wrist joint J1. The first frame 21 and the second frame 22 are hinged at the second rotation axis Y of an additional joint J30. The additional joint J30 is positioned at a portion A of the palmar frame 20 (referring to FIG. 1). The second frame 22 and the operating lever 70 are hinged at the third rotation axis of a joint J2. The actuating lever 50 and the actuating rod 60 are connected at a joint J21. The actuating rod 60 and the operating lever 70 are connected at a joint J22. The operating lever 70 and the finger frame 80 may be hinged at a rotation axis, which is parallel to the third rotation axis X, of the joint J3.

The additional joint J30 may be located at a distal side of the wrist joint J1. The additional joint J30 may be located between the wrist joint J1 and the thumb frame 30.

Figure 4:
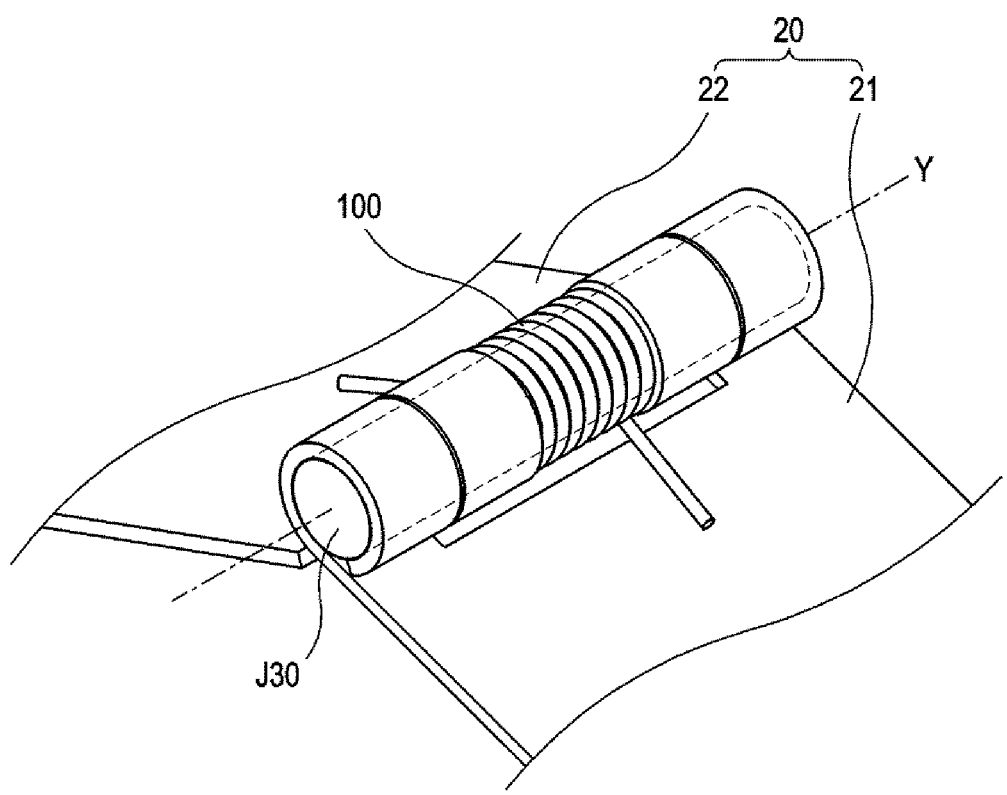
FIG. 4 is a perspective view showing an additional joint J30 according to an embodiment.
Figure 5:
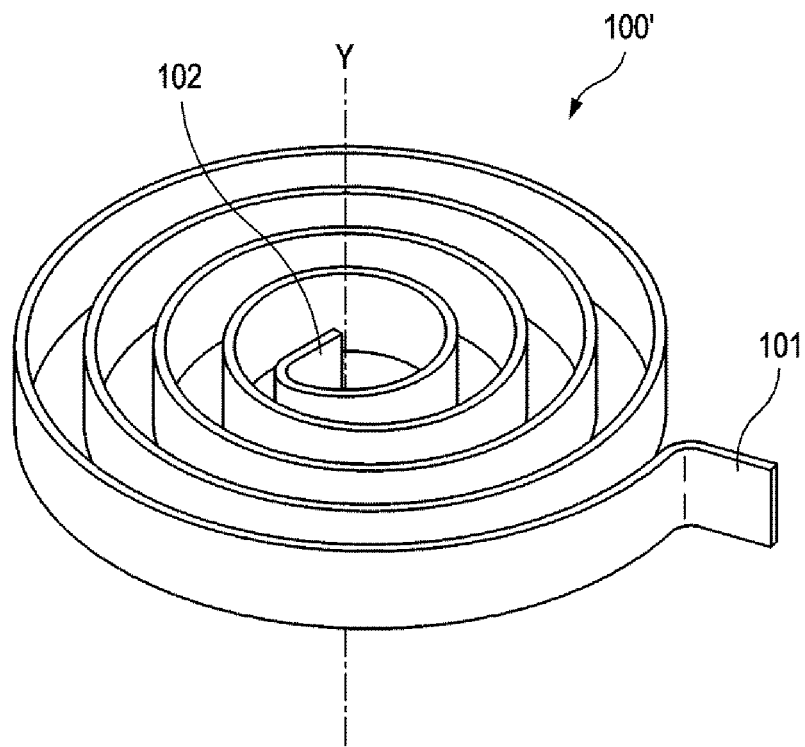
FIG. 5 is a perspective view showing a spring 100' according to another embodiment.

FIG. 4 is a perspective view showing an additional joint J30 according to an embodiment. FIG. 5 is a perspective view showing a spring 100' according to another embodiment. Hereinafter, referring to FIGS. 4 and 5, the flexor hinge orthosis FHO may comprise a spring configured to be elastically deformed when the second frame 22 rotates in a first rotation direction and to be elastically restored when the second frame 22 rotates in a second rotation direction that is opposite to the first rotation direction. The first rotation direction is a rotation direction when a distal end of the second frame 22 moves in radius-side direction. The second rotation direction is a rotation direction when the distal end of the second frame 22 moves in ulna-side direction.

In most cases, a forearm's ulna-side muscle of a paralytic is more paralyzed than a radius-side muscle of the paralytic, and the paralyzed hand tends to rotate in the first rotation direction. The spring can compensate for this tendency.

The spring may be a compression spring or a tension spring. The spring may be a coil spring, torsion bar spring, air spring or leaf spring. The spring may be a torsion spring 100 or a spiral spring 100' referring to FIGS. 4 and 5.

Referring FIG. 5, the spring may be a spiral spring 100'. One end 101 of the spiral spring 100' may be fixed to the second frame 22, and the other end 102 may be fixed to the first frame 21. The spiral spring 100' may be configured such that a degree of winding of the spiral spring 100' is adjustable by a user in a state in which the second frame 22 does not rotate with respect to the first frame 21. Accordingly, the elastic force of the spring 100' according to the rotation angle between the first frame 21 and the second frame 22 can be adjusted.

Figure 6:
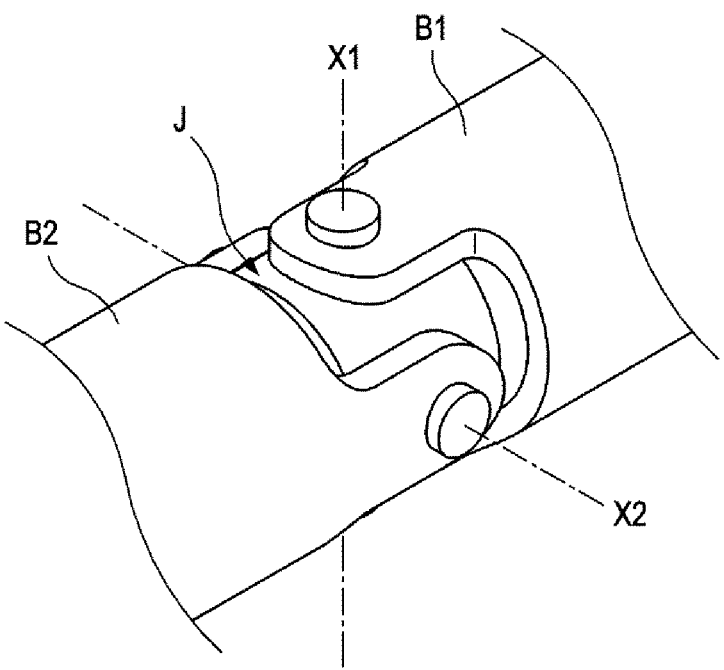
FIG. 6 is a perspective view showing a universal joint J as an actuating joint J21 and/or operating joint J22 according to an embodiment.

FIG. 6 is a perspective view showing a universal joint J as an actuating joint J21 and/or operating joint J22 according to an embodiment. Hereinafter, referring to FIG. 6, the actuating rod 60 and the actuating lever 50 may be connected to each other by a universal joint J21. The actuating rod 60 and the operating lever 70 may be connected to each other by a universal joint J22. In the case that the joint is the joint J21, a member B1 may be the actuating rod 60 and a member B2 may be the actuating lever 50. In the case that the joint is the joint J22, a member B1 may be the actuating rod 60 and a member B2 may be the operating lever 70. The member B1 is connected to the member B2 about a rotation axis X1 and a rotation axis X2. The rotation axis X1 may be perpendicular to the rotation axis X2. The rotation axis X1 and the rotation axis X2 may be disposed at a same plane.

Although the present disclosure has been described in relation to some embodiments, it should be noted that there may be various modifications and changes without departing from the spirit and scope of the present disclosure, which can be understood by those skilled in the art. In addition, such modifications and changes should be construed to belong to the scope of the claims appended herein.

What is claimed is:

1. A flexor hinge orthosis, comprising:
   a forearm frame configured to be fixed to a forearm of a user;
   a first frame connected to the forearm frame such that the first frame is rotatable about a first rotation axis that extends in a first lateral direction;
   a second frame configured to be fixed to a palmar of the user and connected to the first frame such that the second frame is rotatable about a second rotation axis that extends in an upward-and-downward direction;

a thumb frame fixed to the second frame and configured to be fixed to a thumb of the user;

an operating lever connected to the second frame such that the operating lever is rotatable about a third rotation axis that extends in a second lateral direction;

an actuating lever fixed to the forearm frame;

an actuating rod having a first end connected to the actuating lever such that the first end is rotatable and a second end connected to the operating lever such that the second end is rotatable; and a finger frame configured to be fixed to an index finger of the user and connected to the operating lever.

2. The flexor hinge orthosis of claim 1, wherein the first end of the actuating rod is rotatable about a rotation axis parallel to the first rotation axis and a rotation axis parallel to the second rotation axis.

3. The flexor hinge orthosis of claim 2, wherein the second end of the actuating rod is rotatable about a rotation axis parallel to the first rotation axis and a rotation axis parallel to the second rotation axis.

4. The flexor hinge orthosis of claim 1, wherein the forearm frame and the first frame are hinged at the first rotation axis of a wrist joint, wherein the first frame and the second frame are hinged at the second rotation axis of an additional joint, and wherein the additional joint is located at a distal side of the wrist joint.

5. The flexor hinge orthosis of claim 4, wherein the first end of the actuating rod is rotatable about a rotation axis parallel to the first rotation axis and a rotation axis parallel to the second rotation axis, and wherein the second end of the actuating rod is rotatable about a rotation axis parallel to the first rotation axis and a rotation axis parallel to the second rotation axis.

6. The flexor hinge orthosis of claim 5, further comprising a spring configured to be elastically deformed when the second frame rotates in a first rotation direction and to be elastically restored when the second frame rotates in a second rotation direction that is opposite to the first rotation direction, wherein the first rotation direction is a rotation direction when a distal end of the second frame moves in radius-side direction.

7. The flexor hinge orthosis of claim 1, further comprising a spring configured to be elastically deformed when the second frame rotates in a first rotation direction and to be elastically restored when the second frame rotates in a second rotation direction that is opposite to the first rotation direction, wherein the first rotation direction is a rotation direction when a distal end of the second frame moves in radius-side direction.

8. The flexor hinge orthosis of claim 7, wherein the spring is a torsion spring or a spiral spring.

9. The flexor hinge orthosis of claim 7, wherein the spring is a spiral spring that is configured such that a degree of winding of the spiral spring is adjustable by the user in a state in which the second frame does not rotate with respect to the first frame.

10. A wrist-driven flexor hinge orthosis, comprising:

a forearm frame configured to be fixed to a forearm of a user;

a first frame connected to the forearm frame such that the first frame is rotatable about a first rotation axis that extends in a first lateral direction;

a second frame configured to be fixed to a palmar of the user and connected to the first frame such that the second frame is rotatable about a second rotation axis that extends in an upward-and-downward direction;

a thumb frame fixed to the second frame and configured to be fixed to a thumb of the user;

an operating lever connected to the second frame such that the operating lever is rotatable about a third rotation axis that extends in a second lateral direction;

an actuating lever fixed to the forearm frame;

an actuating rod having a first end connected to the actuating lever such that the first end is rotatable and a second end connected to the operating lever such that the second end is rotatable; and a finger frame configured to be fixed to an index finger of the user and connected to the operating lever.

11. The wrist-driven flexor hinge orthosis of claim 10, wherein the first end of the actuating rod is rotatable about a rotation axis parallel to the first rotation axis and a rotation axis parallel to the second rotation axis.

12. The wrist-driven flexor hinge orthosis of claim 11, wherein the second end of the actuating rod is rotatable about a rotation axis parallel to the first rotation axis and a rotation axis parallel to the second rotation axis.

13. The wrist-driven flexor hinge orthosis of claim 10, wherein the forearm frame and the first frame are hinged at the first rotation axis of a wrist joint, wherein the first frame and the second frame are hinged at the second rotation axis of an additional joint, and wherein the additional joint is located at a distal side of the wrist joint.

14. The wrist-driven flexor hinge orthosis of claim 13, wherein the first end of the actuating rod is rotatable about a rotation axis parallel to the first rotation axis and a rotation axis parallel to the second rotation axis, and the second end of the actuating rod is rotatable about a rotation axis parallel to the first rotation axis and a rotation axis parallel to the second rotation axis.

15. The wrist-driven flexor hinge orthosis of claim 14, further comprising a spring configured to be elastically deformed when the second frame rotates in a first rotation direction and to be elastically restored when the second frame rotates in a second rotation direction that is opposite to the first rotation direction, wherein the first rotation direction is a rotation direction when a distal end of the second frame moves in radius-side direction.

16. The wrist-driven flexor hinge orthosis of claim 10, further comprising a spring configured to be elastically deformed when the second frame rotates in a first rotation direction and to be elastically restored when the second frame rotates in a second rotation direction that is opposite to the first rotation direction, wherein the first rotation direction is a rotation direction when a distal end of the second frame moves in radius-side direction.

17. The wrist-driven flexor hinge orthosis of claim 16, wherein the spring is a torsion spring or a spiral spring.

18. The wrist-driven flexor hinge orthosis of claim 16, wherein the spring is a spiral spring that is configured such that a degree of winding of the spiral spring is adjustable by the user in a state in which the second frame does not rotate with respect to the first frame.

* * * * *